US010874659B2

(12) United States Patent
Phadke et al.

(10) Patent No.: US 10,874,659 B2
(45) Date of Patent: Dec. 29, 2020

(54) ILOPERIDONE METABOLITE FOR USE IN THE TREATMENT OF PSYCHIATRIC DISORDERS

(71) Applicant: Vanda Pharmaceuticals, Inc., Washington, DC (US)

(72) Inventors: Deepak Phadke, Olathe, KS (US); Curt D. Wolfgang, Germantown, MD (US); Mihael H. Polymeropoulos, Potomac, MD (US); John Joseph Feeney, Olney, MD (US); Gunther Birznieks, Bethesda, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 0 days.

(21) Appl. No.: 14/384,401

(22) PCT Filed: Mar. 14, 2013

(86) PCT No.: PCT/US2013/031413
§ 371 (c)(1),
(2) Date: Sep. 11, 2014

(87) PCT Pub. No.: WO2013/138602
PCT Pub. Date: Sep. 19, 2013

(65) Prior Publication Data
US 2015/0045390 A1  Feb. 12, 2015

Related U.S. Application Data

(60) Provisional application No. 61/610,664, filed on Mar. 14, 2012.

(51) Int. Cl.
| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/454* | (2006.01) |
| *A61P 25/18* | (2006.01) |

(52) U.S. Cl.
CPC ............ *A61K 31/454* (2013.01); *A61P 25/18* (2018.01)

(58) Field of Classification Search
None
See application file for complete search history.

(56) References Cited

U.S. PATENT DOCUMENTS

| | | |
|---|---|---|
| 5,364,866 A | 11/1994 | Strupczewski et al. |
| 7,977,356 B2 | 7/2011 | Grimler et al. |
| 2007/0197595 A1 | 8/2007 | Nozulak et al. |
| 2009/0306137 A1 | 12/2009 | Wolfgang et al. |

FOREIGN PATENT DOCUMENTS

| | | | |
|---|---|---|---|
| JP | 2005504783 A | 2/2005 | |
| JP | 2006501313 A | 1/2006 | |
| JP | 2006513161 A | 4/2006 | |
| JP | 2009538331 A | 11/2009 | |
| WO | 03020707 A1 | 3/2003 | |
| WO | 03054226 A2 | 7/2003 | |
| WO | 2005030763 A1 | 4/2005 | |
| WO | 2006039663 A2 | 4/2006 | |
| WO | 2008121899 A2 | 10/2008 | |
| WO | 2009036056 A1 | 3/2009 | |
| WO | 2009036100 A2 | 3/2009 | |
| WO | WO 2010030783 A1 * | 3/2010 | ........... A61K 31/454 |
| WO | 2010117931 A1 | 10/2010 | |
| WO | 2010117937 A1 | 10/2010 | |
| WO | 2010117941 A1 | 10/2010 | |
| WO | 2010117943 A1 | 10/2010 | |
| WO | 2010132866 A1 | 11/2010 | |

OTHER PUBLICATIONS

Montes et al., "Iloperidone (Fanapt): An FDA-Approved Treatment Option for Schizophrenia," Pharmacy and Therapeutics. 34(11):606-13 (2009).
Grounds for Rejection for KR Application No. 10-2014-7026434, dated Apr. 1, 2016, 8 pages.
Anonymouse: "FANAPT(tm)" (iloperidone) tablets Highlights of Prescribing Information May 2009, pp. 1-23 XP055276081.
Letter of Dec. 15, 2010 on EP application No. 02767454.8 during examination.
Letter of Feb. 20, 2012 on EP application No. 10009915.9 during examination.
EP application No. 13721817.8 Communication pursuant to Article 94(3) EPC dated Jun. 8, 2016.
Albers et al., "Iloperidone: A new benzisoxazole atypical antipsychotic drug. Is it novel enough to impact the crowded atypical antipsychotic market?," 2008, pp. 61-75, Expert Opinion on Investigational Drugs, Ashley Publications Ltd, vol. 17, No. 1 (XP002493623).
Caccia et al., "New atypical antipsychotics for schizophrenia: Iloperidone," 2010, pp. 33-48, Drug Design, Development and Therapy 2010 Dove Medicall Press Ltd (XP002697976).
Subramanian et al., "Receptor profile of P88-8991 and P95-12113, metabolites of the novel antipsychotic iloperidone," 2002, pp. 553-560, Progress in Neuro-Psychopharmacology & Biological Psychiatry (XP008087896).
Patent Cooperation Treaty, the International Search Report and the Written Opinion of the International Searching Authority, or the Declaration for PCT/US2013/031413 dated Jun. 13, 2013, 13 pages.
Takahashi et al., "Drug therapy for sleep apnea syndrome", Nihon Rinsho, Japanese Journal of Clinical Medicine, vol. 58, Aug. 1, 2000, Abstract only translated.
Takahashi et al., "Drug therapy for sleep apnea syndrome", Nihon Rinsho, Japanese Journal of Clinical Medicine, vol. 58, Aug. 1, 2000, 4 pages.
Japanese Clinic, "Memory Table Advertisement Column," 69(7), 2011.
Kasahara et al., "Presenile and senile affective disorders," 52(5, 127-133, 1994 .

(Continued)

*Primary Examiner* — Layla Soroush
(74) *Attorney, Agent, or Firm* — Hoffman Warnick LLC

(57) ABSTRACT

R-P88 is used for the treatment of disorders amenable to treatment with an atypical antipsychotic.

7 Claims, No Drawings

(56) References Cited

OTHER PUBLICATIONS

English Translation of Japanese Final Office for Application No. P2016-217680, dated May 8, 2018, 4 pages.
Takahashi et al., "Drug therapy for sleep apnea syndrome," 107(1671)-110(1674), 2000, 5 pages.
Office Action for Russian Patent Application No. 2014 141 112, dated May 31, 2016, 22 pages.
"A Short Course of Molecular Pharmacology" edit. by P. V. Sergeev, M., 1975, p. 10.
L. E. Kholodov et al., "Clinical Pharmacokinetics", M., "Medicine", 1985, pp. 83-98, 134-138, 160, 378-380.

* cited by examiner

ILOPERIDONE METABOLITE FOR USE IN THE TREATMENT OF PSYCHIATRIC DISORDERS

CROSS-REFERENCE TO RELATED APPLICATIONS

This application claims the benefit of U.S. Provisional Patent Application No. 61/610,664, filed 14 Mar. 2012, which is hereby incorporated herein.

FIELD OF THE INVENTION

This invention is in the field of treatment of disorders amenable to treatment with an atypical antipsychotic such as iloperidone.

BACKGROUND OF THE INVENTION

Iloperidone (1-[4-[3-[4-(6-flouro-1,2-benzisoxazol-3-yl)-1-piperidinyl]propoxy]-3-methoxyphenyl] ethanone) is disclosed in U.S. Pat. No. 5,364,866, which is incorporated herein by reference. Active metabolites of Iloperidone, e.g., S-P88 (also referred to as (S)-P-88-8891), are useful in the present invention. See, e.g., WO2003020707, which is incorporated herein by reference. In some cases, it may be advantageous to use iloperidone preferentially in patients with certain genotypes as disclosed, e.g., in WO2006039663 and in WO2003054226, which are incorporated herein by reference.

Fanapt® iloperidone is currently approved in the United States for the acute treatment of schizophrenia. The recommended target dosage of Fanapt® tablets is 12 to 24 mg/day, administered b.i.d., i.e., twice per day. The target dosing range is achieved by daily dosage adjustments, alerting patients to symptoms of orthostatic hypotension. Fanapt® must be titrated slowly from a low starting dose to avoid orthostatic hypotension due to its alpha adrenergic blocking properties. The recommended starting dose for Fanapt® tablets is 1 mg taken twice daily. Increases to reach the target dose range of 6-12 mg twice daily, may be made with daily dosage adjustments to 2 mg twice daily, 4 mg twice daily, 6 mg twice daily, 8 mg twice daily, 10 mg twice daily, and 12 mg twice daily on days 2, 3, 4, 5, 6, and 7, respectively. The maximum recommended dose is 12 mg twice daily (24 mg/day).

SUMMARY OF THE INVENTION

This invention relates to the treatment of disorders that are amenable to treatment with an atypical antipsychotic, in particular, iloperidone, that comprises administering to the patient R-P88 according to a dosing that is derived from the pharmacokinetics of R-P88 in the body.

In a particular illustrative embodiment, the invention provides a method of treating a patient suffering from a disorder amenable to treatment with iloperidone that comprises internally administering to the patient an effective amount of R-P88 once per day.

In another embodiment, the invention provides a method of treating a patient suffering from a disorder amenable to treatment with iloperidone that comprises internally administering to the patient an effective amount of R-P88 twice per day, wherein the effective amount is 3 to 9 mg twice daily (totaling 6 to 18 mg/day.

The illustrative aspects of the present invention are designed to solve the problems herein described and other problems not discussed, which are discoverable by a skilled artisan.

DETAILED DESCRIPTION OF THE INVENTION

There are three major metabolic pathways by which iloperidone is cleared in humans. Specifically, iloperidone is:

(1) converted to S-P88, which both (a) converts back to iloperidone, creating a dynamic equilibrium (P88 ⇔ Iloperidone), and (b) is further metabolized and eliminated via the CYP2D6 pathway;
(2) metabolized via the CYP2D6 pathway to P95, which is then eliminated;
(3) metabolized via the CYP3A4 pathway to P89, which is then eliminated.

This invention relates to a method of treating a patient suffering from a disorder that is amenable to treatment with an antipsychotic, such as iloperidone, that comprises orally administering R-P88.

P88, by its chemical name, is known as 1-[4-[3-[4-(6-Fluoro-1,2-benzisoxazol-3-yl)-1-piperidinyl]propoxyl-3-methoxyphenyl]ethanol and, alternatively, as 4-[3-[4-(6-Fluoro-1,2-benzisoxazol-3-yl)-1-piperidinyl]propoxy]-3-methoxy-a-methylbenzenemethanol. In humans, P-88 is found only in the S-enantiomeric form, which has the following structure:

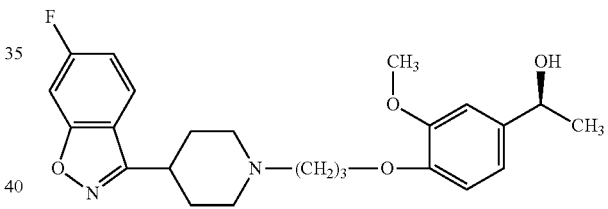

However, P-88 can also be synthesized in its R enantiomeric form, which has the structure:

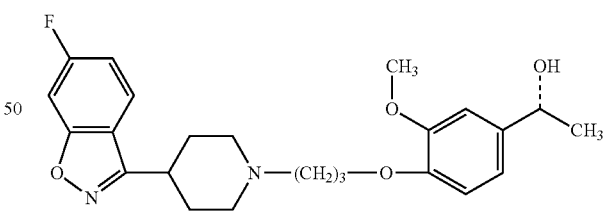

P88 and the S and R forms thereof are described in U.S. Pat. No. 7,977,356, which is incorporated herein by reference as though fully set forth.

Although R-P88 is not found in humans, it has a receptor binding profile for relevant receptors that is similar to that of iloperidone and S-P88 in important ways and is therefore useful as an atypical antipsychotic.

In human plasma, in vitro, R-P88 converts back to iloperidone more slowly than does S-P88. This invention takes advantage of this unexpected finding by using R-P88 in place of iloperidone, or in place of racemic P88 or S-P88, in the treatment of conditions for which an atypical antipsychotic is indicated. Specifically, while iloperidone is administered twice per day at a maximum daily dose of 24 mg/day, R-P88 can be administered once per day or, at lower doses than iloperidone (or S-P88), twice per day Thus, in an illustrative aspect of this invention, an effective amount of R-P88, or a salt or solvate thereof, is orally administered to a human suffering from a psychiatric disorder, e.g., schizophrenia, schizoaffective disorder, bipolar disorder (mania and/or depression), depression, major depression, psychotic episodes, autism, autism spectrum disorder, fragile X syndrome, and pervasive developmental disorder. An effective amount is an amount that during the course of therapy will have a preventive or ameliorative effect on a psychiatric disorder, such as schizophrenia, or a symptom thereof, or of bipolar disorder. An effective amount, quantitatively, may vary depending upon, for example, the patient, the severity of the disorder or symptom being treated, and the route of administration.

It will be understood that the dosing protocol including the amount of R-P88 or salt or solvate thereof actually administered will be determined by a qualified healthcare professional in the light of the relevant circumstances including, for example, the condition to be treated, the chosen route of administration, the age, weight, and response of the individual patient, and the severity of the patient's symptoms. Patients should of course be monitored for possible adverse events, including, e.g., those adverse events associated with administration of iloperidone, e.g., QT prolongation and orthostatic hypotension.

q.d. Dosing Protocols

In an illustrative embodiment of the invention, the patient swallows a pharmaceutical composition comprising an effective amount of R-P88 once per day (q.d.), e.g., in an amount of 1 to 24 mg/day, 6 to 24 mg/day, 12 to 24 mg/day, 6 to 18 mg/day, or 6 to 12 mg/day, e.g., 1, 2, 3, 4, 5, 6, 7, 8, 9, 10, 11, 12, 14, 16, 18, 20, 22, or 24 mg/day. At the initiation of treatment, the amount of R-P88 administered each day can be titrated upwards until a final dose, i.e., a maximum dose, is reached, similar to the way in which iloperidone is titrated upon initiation of treatment. For example, a patient can be administered R-P88 once per day titrated in accordance with the following increments:

1 mg once daily, 2 mg once daily, 4 mg once daily, 6 mg once daily, 8 mg once daily, 10 mg once daily, 12 mg once daily, to reach a maximum, i.e., final, dose of 12 mg/day, or 2 mg once daily, 4 mg once daily, 8 mg once daily, 12 mg once daily, 16 mg once daily, 20 mg once daily, 24 mg once daily, to reach a maximum dose of 24 mg/day, or 2 mg once daily, 4 mg once daily, 8 mg once daily, 12 mg once daily, to reach a maximum dose of 12 mg/day.

In other illustrative q.d. dosing protocols of the invention, upward titration to a final dose may be made more quickly, e.g., more quickly than for iloperidone, or upward titration may be omitted entirely, with a final dose administered to a patient at the first administration. For example, in an illustrative embodiment of the invention, an abbreviated upward titration may include:

1 mg once daily, 4 mg once daily, 8 mg once daily, and 12 mg once daily, on days 1, 2, 3, and 4 to reach a maximum dose of 12 mg/day, or 2 mg once daily, 6 mg once daily, and 12 mg once daily, on days 1, 2, and 3 to reach a maximum dose of 12 mg/day, or 4 mg once daily, 8 mg once daily, 16 mg once daily, and 24 mg once daily, on days 1, 2, 3, and 4 to reach a maximum dose of 24 mg/day, or 8 mg once daily and 24 mg once daily, on days 1 and 2 to reach a maximum dose of 24 mg/day.

Thus, illustrative titration schedules for q.d. administration include, e.g.:

1 mg q.d. on day 1, 2 mg q.d. on day 2, 4 mg q.d. on day 3, 6 mg q.d. on day 4, 8 mg q.d. on day 5, 10 mg q.d. on day 6, and 12 mg q.d. on day 7 and thereafter, or 2 mg q.d. on day 1, 4 mg q.d. on day 2, 8 mg q.d. on day 3, 12 mg q.d. on day 4, 16 mg q.d. on day 5, 20 mg q.d. on day 6, and 24 mg q.d. on day 7 and thereafter, or 2 mg q.d. on days 1 and 2, 4 mg q.d. on days 3 and 4, 8 mg q.d. on days 5 and 6, and 12 mg q.d. on day 7 and thereafter, 1 mg q.d. on day 1, 4 mg q.d. on day 2, 8 mg q.d. on day 3, and 12 mg q.d. on day 4 and thereafter, or 2 mg q.d. on days 1 and 2, 6 mg q.d. on days 3 and 4, and 12 mg q.d. on day 5 and thereafter, or 4 mg q.d. on day 1, 8 mg q.d. on day 2, 16 mg q.d. on day 3, and 24 mg q.d. on day 4 and thereafter, or 8 mg q.d. on days 1 and 2 and 24 mg q.d. on day 3 and thereafter.

b.i.d. Dosing Protocols

In an illustrative embodiment of the invention, the patient swallows a pharmaceutical composition comprising an effective amount of R-P88 twice per day (bid.) in the amount of 1 to 24 mg/day, e.g., 2 to 18 mg/day, e.g., 6 to 18 mg/day, e.g., 6 mg/day, 12 mg/day, 16 mg/day, or 18 mg/day. In such illustrative embodiment, at the initiation of treatment, the amount R-P88 administered each day can be titrated upwards until a final dose is reached. For example, a patient can be administered R-P88 once per day titrated in accordance with the following increments:

1 mg twice daily, 2 mg twice daily, and 3 mg twice daily, to reach a maximum dose of 6 mg/day, or 1 mg twice daily, 2 mg twice daily, 3 mg twice daily, 4 mg twice daily, 5 mg twice daily and 6 mg twice daily, to reach a maximum dose of 12 mg/day, or 1 mg twice daily, 2 mg twice daily, 4 mg twice daily, 6 mg twice daily, 8 mg twice daily, to reach a maximum dose of 16 mg/day, or 1 mg twice daily, 2 mg twice daily, 4 mg twice daily, 6 mg twice daily, 8 mg twice daily, 10 mg twice daily, and 12 mg twice daily, to reach a maximum dose of 24 mg/day.

In other illustrative b.i.d. dosing protocols of the invention, upward titration to a final dose may be made more quickly, e.g., more quickly than for iloperidone, or upward titration may be omitted entirely, with a final dose administered to a patient at the first administration. For example, in an illustrative embodiment of the invention, an abbreviated upward titration may include:

1 mg twice daily, 4 mg twice daily, and 6 mg twice daily, on days 1, 2, 3, and 4 to reach a maximum dose of 12 mg/day, or 2 mg twice daily and 6 mg twice daily, on days 1 and 2 to reach a maximum dose of 12 mg/day, or 1 mg twice daily, 4 mg twice daily, and 12 mg twice daily, on days 1, 2, and 3 to reach a maximum dose of 24 mg/day, or 2 mg twice daily, 6 mg twice daily, and 12 mg twice daily, on days 1, 2, and 3 to reach a maximum dose of 24 mg/day.

Thus, illustrative titration schedules for ba.d. administration include, e.g.:

1 mg b.i.d. on day 1, 2 mg b.i.d. on day 2, 3 mg b.i.d. on day 3 and thereafter or 1 mg b.i.d. on day 1, 2 mg b.i.d. on day 2, 3 mg b.i.d. on day 3, 4 mg b.i.d. on day 4, 5 mg b.i.d. on day 5, 6 mg b.i.d. on day 6 and thereafter or 1 mg b.i.d. on day 1, 2 mg b.i.d. on day 2, 4 mg b.i.d. on day 3, 6 mg b.i.d. on day 4, 8 mg b.i.d. on day 5 and thereafter or 1 mg b.i.d. on day 1, 2 mg b.i.d. on day 2, 4 mg b.i.d. on day 3, 6 mg b.i.d. on day 4, 8 mg b.i.d. on day 5, 10 mg b.i.d. on day 6, 12 mg b.i.d. in day 7 and thereafter.

Pharmaceutical Compositions & Administration

For therapeutic or prophylactic use, R-P88 or a salt or solvate thereof will normally be administered as a pharmaceutical composition comprising R-P88 as the (or an) essential active pharmaceutical ingredient with a solid or liquid pharmaceutically acceptable carrier and, optionally, with pharmaceutically acceptable excipients employing standard and conventional techniques.

Pharmaceutical compositions useful in the practice of this invention include suitable dosage forms for oral administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents.

The pharmaceutical compositions may be prepared by conventional techniques appropriate to the desired preparation containing appropriate amounts of R-P88. See, for example, Remington's Pharmaceutical Sciences, Mack Publishing Company, Easton, Pa., 17th edition, 1985.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions can be formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier. Such unit dosage form can be formulated with an amount of R-P88 required to administer R-P88 in accordance with any of the dosing protocols described in this specification or claims. For example, if a patient is being treated with R-P88, 6 mg/day b.i.d., each unit dosage form can comprise 6 mg of R-P88 and the patient would take one unit dose form in the morning and one in the afternoon or evening. Or, if a patient is being treated with R-P88, 12 mg/day b.i.d., each unit dosage form can comprise 6 mg of R-P88 and the patient would take two unit dosage forms in the morning and two in the afternoon or evening.

Methods for the administration of iloperidone directed toward, inter alia, eliminating or minimizing the prolongation of a corrected electrocardiographic QT (QTc) interval associated with increased concentrations of iloperidone or iloperidone derivatives are described in WO 2006/039663, WO 2008/121899, WO 2009/036056, WO 2009/036100, WO 2010/117931, WO 2010/117937, WO 2010/117941, WO 2010/117943, and WO2010/132866, all of which are incorporated herein by reference. Such methods can also be applied to R-P88 administered in accordance with the method of this invention.

The invention thus includes R-P88, as well as a pharmaceutical composition comprising R-P88, for the treatment of disorders that are amenable to treatment with an atypical antipsychotic in accordance with the dosing regiments generally and specifically described above.

Synthesis

R-P88 can be synthesized by known methods, such as those disclosed in U.S. Pat. No. 7,977,356. As disclosed therein, R-P88 can be synthesized by the stereospecific reduction of iloperidone, which has formula III:

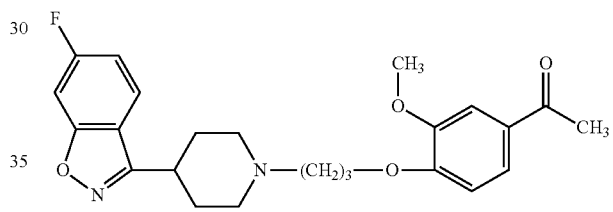

with an optically active borane complex of formula IV:

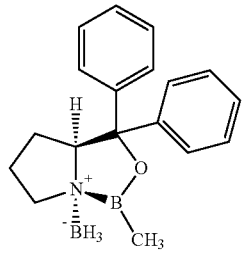

The reactions can be effected according to conventional methods. Working up the reaction mixtures and purification of the compounds thus obtained may be carried out in accordance with known procedures.

Acid addition salts may be produced from the free bases in known manner, and vice-versa. Suitable acid addition salts for use in accordance with the present invention include, for example, the hydrochloride.

The borane complexes used as starting materials can be produced from the corresponding compounds of formulas Va and Vb, according to known procedures.

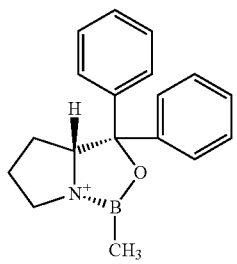

Va

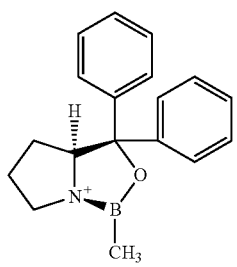

Vb

The starting materials of formulas Va and Vb are known.

EXAMPLE

The aim of this study was to evaluate the potential conversion of (R)-P88 and (S)-P88 to iloperidone in human liver S9 fraction in the presence of NAD and NADP. A copy of the final report from this study, entitled, "InVitro Metabolism of (R)-P88 and (S)-P88 in Human Liver S9 Fraction," ("Final Report") is attached.

Three concentrations of (R)-P88 and (S)-P88 (1, 10 and 100 µM) were incubated with human liver S9 fractions in the presence of NAD and NADP. Under initial rate conditions, 13 concentrations of (R)-P88 and (S)-P88 (1 to 100 µM) were incubated with human liver S9 fractions to determine the Michaelis-Menten enzyme kinetic constants, Km and Vmax, for the formation of iloperidone.

The resultant data showed that S-P88 converted significantly more quickly to iloperidone than did R-P88. At some substrate concentrations, the rate of R-P88 conversion to iloperidone was more than twice that of S-P88 to iloperidone. The data, which were statistically significant, are shown in the following table.

| Substrate Conc. | Mean Rate of Iloperidone Formation (pmol/ min/mg protein) | | Difference Between | p value | 95% Confidence Interval for Difference |
|---|---|---|---|---|---|
| µ(µM) | R-P88 | S-P88 | Means | | Between Means |
| 1 | 15.5 | 36.3 | 20.8 | <0.001 | 19.8 to 21.8 |
| 2 | 29.8 | 62.1 | 32.4 | <0.001 | 23.5 to 41.2 |
| 4 | 66.3 | 101 | 34.9 | 0.002 | 22.3 to 47.6 |
| 6 | 87.4 | 167 | 79.9 | <0.001 | 61.7 to 98.1 |
| 8 | 126 | 183 | 57.4 | 0.002 | 35.1 to 79.8 |
| 10 | 158 | 271 | 112 | <0.001 | 104 to 121 |
| 12.5 | 186 | 298 | 112 | <0.001 | 96.1 to 128 |
| 15 | 211 | 340 | 130 | <0.001 | 117 to 143 |
| 20 | 262 | 439 | 176 | <0.001 | 142 to 211 |
| 25 | 307 | 553 | 247 | <0.001 | 207 to 287 |
| 50 | 423 | 922 | 499 | <0.001 | 392 to 606 |
| 75 | 491 | 1270 | 776 | <0.001 | 715 to 837 |
| 100 | 521 | 1660 | 1139 | <0.001 | 954 to 1324 |

In addition, results of the experiments include that the conversion of (R)-P88 to iloperidone showed a slightly S-shaped direct plot and "hook"-shaped Eadie-Hofstee plot suggesting allosteric interactions.

In contrast, the conversion of (S)-P88 to iloperidone best fit a biphasic saturation enzyme model suggesting two enzymes contributing to the metabolism of (S)-P88, one high-affinity enzyme with normal saturation kinetics and one low affinity enzyme with linear (non-saturating) enzyme kinetics.

In addition, slower conversion of R-P88 to iloperidone is expected to result in decreased formation of P95, which has the following structure and chemical name:

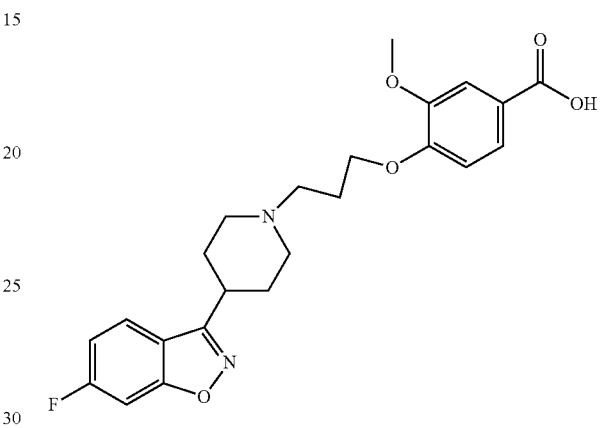

4-[3-[4-(6-Fluoro-1,2-benzisoxazol-3-yl)-1-piperidinyl] propoxyl-3-methoxy-benzoic acid, and which has been implicated in episodes of orthostatic hypotension following initial administration of iloperidone.

R-P88 may form pharmaceutically acceptable salts. It may also form fatty acid esters, e.g., via the hydroxy group in the ethanolic moiety, and pharmaceutically acceptable salts thereof, such as described in US20070197595, which is incorporated herein by reference. This invention comprises use of such salts, esters, or salts of esters in place of or in addition to R-P88.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of treating a patient suffering from a psychiatric disorder that comprises internally administering to the patient R-P88, or a pharmaceutically acceptable salt thereof, or an ester of R-P88, or a pharmaceutically acceptable salt of such ester, once per day, titrated to a final dose in accordance with one of the following increments:
   1 mg once daily, 2 mg once daily, 4 mg once daily, 6 mg once daily, 8 mg once daily, 10 mg once daily, 12 mg once daily, to reach a maximum dose of 12 mg/day; or
   2 mg once daily, 4 mg once daily, 8 mg once daily, 12 mg once daily, to reach a maximum dose of 12 mg/day; or
   1 mg once daily, 4 mg once daily, 8 mg once daily, and 12 mg once daily, to reach a maximum dose of 12 mg/day; or
   2 mg once daily, 6 mg once daily, and 12 mg once daily, to reach a maximum dose of 12 mg/day.

2. The method of claim 1 wherein the disorder is one that is amenable to treatment with iloperidone.

3. The method of claim 1 wherein the disorder is one or more of schizophrenia, schizoaffective disorder, bipolar disorder (mania and/or depression), depression, major depression, psychotic episodes, autism, autism spectrum disorder, fragile X syndrome, and pervasive developmental disorder.

4. The method of claim 1, wherein the R-P88, or the pharmaceutically acceptable salt thereof, or the ester of R-P88, or the pharmaceutically acceptable salt of such ester, is orally administered.

5. A method of treating a patient suffering from a psychiatric disorder that comprises internally administering to the patient R-P88, or a pharmaceutically acceptable salt thereof, or an ester of R-P88, or a pharmaceutically acceptable salt of such ester, twice per day, titrated in accordance with one of the following increments:
   1 mg twice daily, 2 mg twice daily, and 3 mg twice daily, to reach a maximum dose of 6 mg/day; or
   1 mg twice daily, 2 mg twice daily, 3 mg twice daily, 4 mg twice daily, 5 mg twice daily and 6 mg twice daily, to reach a maximum dose of 12 mg/day; or
   1 mg twice daily, 2 mg twice daily, 4 mg twice daily, 6 mg twice daily, 8 mg twice daily, to reach a maximum dose of 16 mg/day; or
   1 mg twice daily, 4 mg twice daily, and 6 mg twice daily, to reach a maximum dose of 12 mg/day; or
   2 mg twice daily and 6 mg twice daily, to reach a maximum dose of 12 mg/day.

6. The method of claim 5 wherein the disorder is one that is amenable to treatment with iloperidone.

7. The method of claim 5, wherein the R-P88, or pharmaceutically acceptable salt thereof, or ester of R-P88, or pharmaceutically acceptable salt of such ester, is titrated in accordance with the following schedule:
   1 mg b.i.d. on day 1, 2 mg b.i.d. on day 2, 3 mg b.i.d. on day 3 and thereafter; or
   1 mg b.i.d. on day 1, 2 mg b.i.d. on day 2, 3 mg b.i.d. on day 3, 4 mg b.i.d. on day 4, 5 mg b.i.d. on day 5, 6 mg b.i.d. on day 6 and thereafter; or
   1 mg b.i.d. on day 1, 2 mg b.i.d. on day 2, 4 mg b.i.d. on day 3, 6 mg b.i.d. on day 4, 8 mg b.i.d. on day 5 and thereafter.

* * * * *